United States Patent
Arnin et al.

(10) Patent No.: US 7,550,009 B2
(45) Date of Patent: Jun. 23, 2009

(54) SPINAL PROSTHESIS

(75) Inventors: Uri Arnin, Kiryat Tivon (IL); Yuri Sudin, Lod (IL); Shai Fleischer, Haifa (IL)

(73) Assignee: Impliant Ltd., Ramat Poleg (IL)

( * ) Notice: Subject to any disclaimer, the term of this patent is extended or adjusted under 35 U.S.C. 154(b) by 472 days.

(21) Appl. No.: 10/898,229

(22) Filed: Jul. 26, 2004

(65) Prior Publication Data

US 2005/0197705 A1 Sep. 8, 2005

Related U.S. Application Data

(60) Provisional application No. 60/550,306, filed on Mar. 8, 2004.

(51) Int. Cl.
*A61F 2/44* (2006.01)
(52) U.S. Cl. .................................................. 623/17.15
(58) Field of Classification Search ... 623/17.11–17.16; 606/61
See application file for complete search history.

(56) References Cited

U.S. PATENT DOCUMENTS

| | | | | |
|---|---|---|---|---|
| 4,759,766 A | * | 7/1988 | Buettner-Janz et al. | 623/17.15 |
| 5,425,773 A | * | 6/1995 | Boyd et al. | 623/17.15 |
| 5,562,738 A | * | 10/1996 | Boyd et al. | 623/17.15 |
| 5,676,701 A | * | 10/1997 | Yuan et al. | 623/17.15 |
| 5,899,941 A | | 5/1999 | Koichi et al. | |
| 6,440,168 B1 | * | 8/2002 | Cauthen | 623/17.14 |
| 6,706,068 B2 | * | 3/2004 | Ferree | 623/17.11 |
| 7,083,649 B2 | * | 8/2006 | Zucherman et al. | 623/17.11 |
| 7,083,651 B2 | * | 8/2006 | Diaz et al. | 623/17.13 |
| 7,204,853 B2 | * | 4/2007 | Gordon et al. | 623/17.16 |

FOREIGN PATENT DOCUMENTS

WO    WO 00/04851    2/2000
WO    WO 03/084449    10/2003

* cited by examiner

*Primary Examiner*—Pedro Philogene
(74) *Attorney, Agent, or Firm*—Dekel Patent Ltd.; David Klein (57) ABSTRACT

An endoprosthesis including a first articulating member formed with a generally concave articulating surface, and a second articulating member formed with a generally convex articulating surface which articulates with the concave articulating surface, the first and second articulating members each having a generally planar attachment surface for attachment to spine structure, wherein the first articulating member includes a contour defined by a cutting surface that cuts through a portion of the first articulating member at a non-zero angle relative to its attachment surface, and the second articulating member includes a contour defined by a cutting surface that cuts through a portion of the second articulating member at a non-zero angle relative to its attachment surface.

12 Claims, 10 Drawing Sheets

SPINAL PROSTHESIS

CROSS-REFERENCE TO RELATED APPLICATIONS

This application claims priority under 35 USC § 119 to U.S. Provisional Patent Application Serial No. 60/550,306, filed on Mar. 8, 2004, which is incorporated herein by reference.

FIELD OF THE INVENTION

The present invention relates to apparatus and methods for spinal prostheses.

BACKGROUND OF THE INVENTION

Spinal disc or partial spinal disc replacement is a common procedure in Europe with thousands having been performed already and is now commencing in the United States. Examples of such replacement discs are ProDisc (Spine Solutions, Inc.) and SB Charite III (Link Spine Group, Inc.)

By replacing a disc and not merely fusing vertebrae, which is the common alternative practice to disc replacement, the mobility of the patient's adjacent discs may be preserved and thus may delay the onset of arthritic changes to adjacent vertebrae.

A typical disc replacement unit is approximately 30 millimeters in diameter. This relatively large cross-section usually necessitates a mostly anterior retroperitoneal (from the front of the abdomen but staying outside the intestinal sac) approach to the spine which may be risky. The risks of general anesthesia are coupled with risks of vascular injury and retrograde ejaculation in males.

Although many prosthetic disc devices are described in the literature, there is still a need for improvement in ease of manufacture and performance.

SUMMARY OF THE INVENTION

The present invention is directed to a spinal prosthesis, as is described more in detail hereinbelow.

There is thus provided in accordance with an embodiment of the present invention an endoprosthesis including a first articulating member formed with a generally concave articulating surface, and a second articulating member formed with a generally convex articulating surface which articulates with the concave articulating surface, the first and second articulating members each having a generally planar attachment surface for attachment to spine structure, wherein the first articulating member includes a contour defined by a cutting surface that cuts through a portion of the first articulating member at a non-zero angle relative to its attachment surface, and the second articulating member includes a contour defined by a cutting surface that cuts through a portion of the second articulating member at a non-zero angle relative to its attachment surface.

The endoprosthesis can include one or more of the following features. For example, the contours may be defined by cutting a sphere. For example, the cutting surfaces may define a "half-moon" shaped contour, a rectangular contour, a cylindrical contour, a bullet-shaped contour, a trapezoidal contour, an oval contour and/or a semi-toroidal contour.

The radii of curvature of the first and second articulating members may or may not generally match. The contact areas of the first and second articulating members may or may not generally match. One of the articulating members may include an articulating portion mounted in a recess formed in an attachment portion. Alternatively, one of the articulating members may include an attachment portion mounted in a recess formed in an articulating portion. The attachment surfaces may include protrusions to improve attachment to the spine structure. The first articulation member may include a plurality of bulbous articulation surfaces which articulate with the second articulation member. An elastomeric member may be positioned between the first and second articulation members. One of the articulation members may include a varying height element whose protrusion from its attachment surface is adjustable.

There is also provided in accordance with an embodiment of the present invention an endoprosthesis including first and second articulating members formed with generally planar attachment surfaces on their outer surfaces that articulate against a third articulation member on their inner surfaces, the first and second articulating members each having a generally planar attachment surface for attachment to spine structure, wherein the first articulating member includes a contour defined by a cutting surface that cuts through a portion of the first articulating member at a non-zero angle relative to its attachment surface, and the second articulating member includes a contour defined by a cutting surface that cuts through a portion of the second articulating member at a non-zero angle relative to its attachment surface.

The inner surfaces of the first and second articulation members may have a convex shape and the third articulation member has a concave shaped articulation surface. The third articulation member may be constructed as a hollow member.

DESCRIPTION OF EMBODIMENTS

Figure 1A:
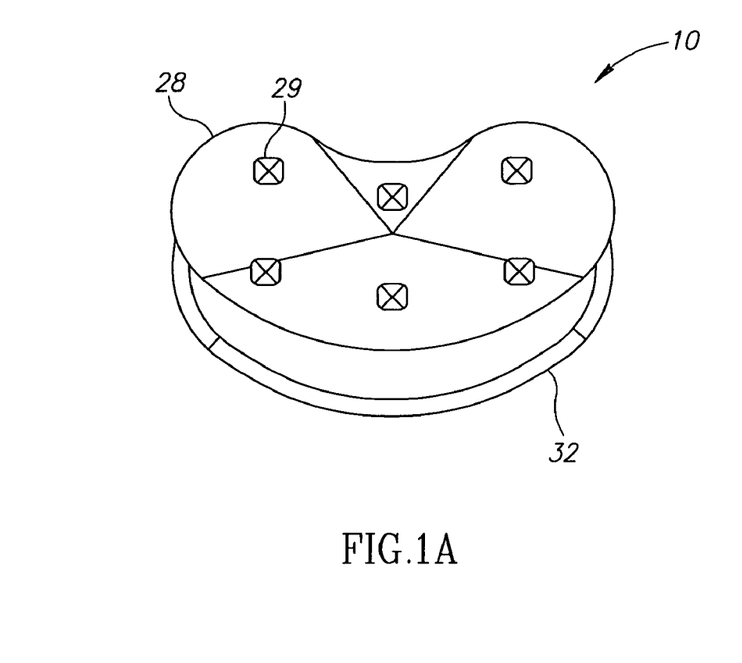
FIGS. 1A and 1B are simplified perspective top view and exploded view illustrations, respectively, of an endoprosthesis, constructed and operative in accordance with an embodiment of the present invention.
Figure 1B:
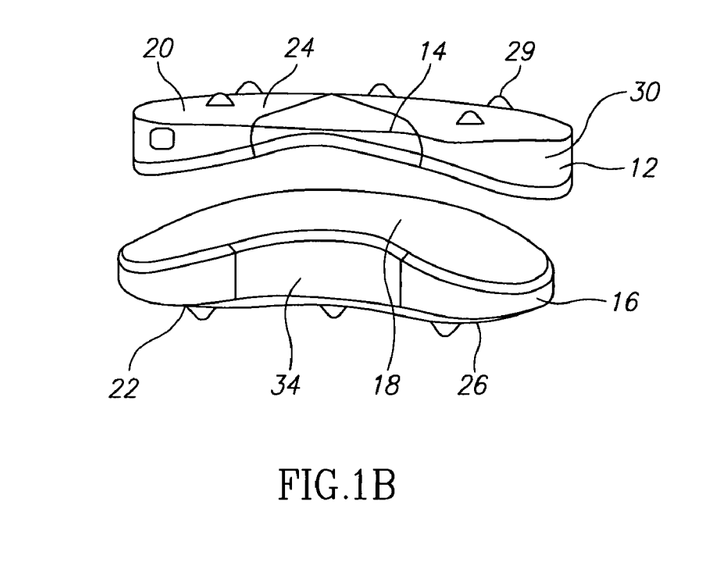

Reference is now made to FIGS. 1A and 1B, which illustrate a vertebral disc endoprosthesis 10, constructed and operative in accordance with an embodiment of the present invention. Endoprosthesis 10 may be fashioned from any combination of materials used for spinal prostheses, such as but not limited to, ceramic, aluminum oxide, zirconium oxide, metal, metal alloy, cobalt-chromium-tungsten-nickel alloy, cobalt-chromium-manganese alloy, cobalt-chromium alloy, cobalt-chromium-molybdenum alloy, chromium-nickel-manganese alloy, powder metal alloy, 316L stainless steel, Ti 6A1-4V ELI, polymer, polyurethane, polyethylene, wear resistant polyethylene, cross-linked polyethylene, thermoplastic elastomer, biomaterial, polycaprolactone, diffusion hardened material, Ti-13-13, zirconium alloy, niobium alloy, with or without a porous coating system, hydrophilic coating system, hydroxyapatite coating system, and tri-calcium phosphate coating system.

Endoprosthesis 10 may be made from at least two or more parts wherein there are two articulating parts.

In accordance with a non-limiting embodiment of the invention, endoprosthesis 10 may include a first articulating member 12 formed with a generally concave articulating surface 14, and a second articulating member 16 formed with a generally convex articulating surface 18 which articulates with concave articulating surface 14. The first and second articulating members 12 and 16 may have generally planar attachment surfaces 20 and 22, respectively, for attachment to structure of the spine. The attachment surface 20 may be generally flat, being defined by a plane 24 (e.g., a horizontal plane) that cuts through and truncates a portion of first articulating member 12 distanced from articulating surface 14. Likewise, the attachment surface 22 may be generally flat, being defined by another plane 26 (e.g., a horizontal plane) that cuts through and truncates a portion of second articulating member 16 distanced from articulating surface 18.

The attachment surfaces 20 and 22 may include spikes or other protrusions 29 to improve the attachment to the spine structure.

In accordance with a non-limiting embodiment of the invention, the first articulating member 12 includes a contour 28 defined by a cutting surface 30 that cuts through another portion of first articulating member 12 at a non-zero angle relative to the plane 24. Similarly, the second articulating member 16 includes a contour 32 defined by a cutting surface 34 that cuts through another portion of second articulating member 16 at a non-zero angle relative to the plane 26. For example, the cutting surfaces 30 and 34 may cut a "half-moon" or "banana" shape that defines contours 28 and 32 of first and second articulating members 12 and 16, respectively.

Figure 2:
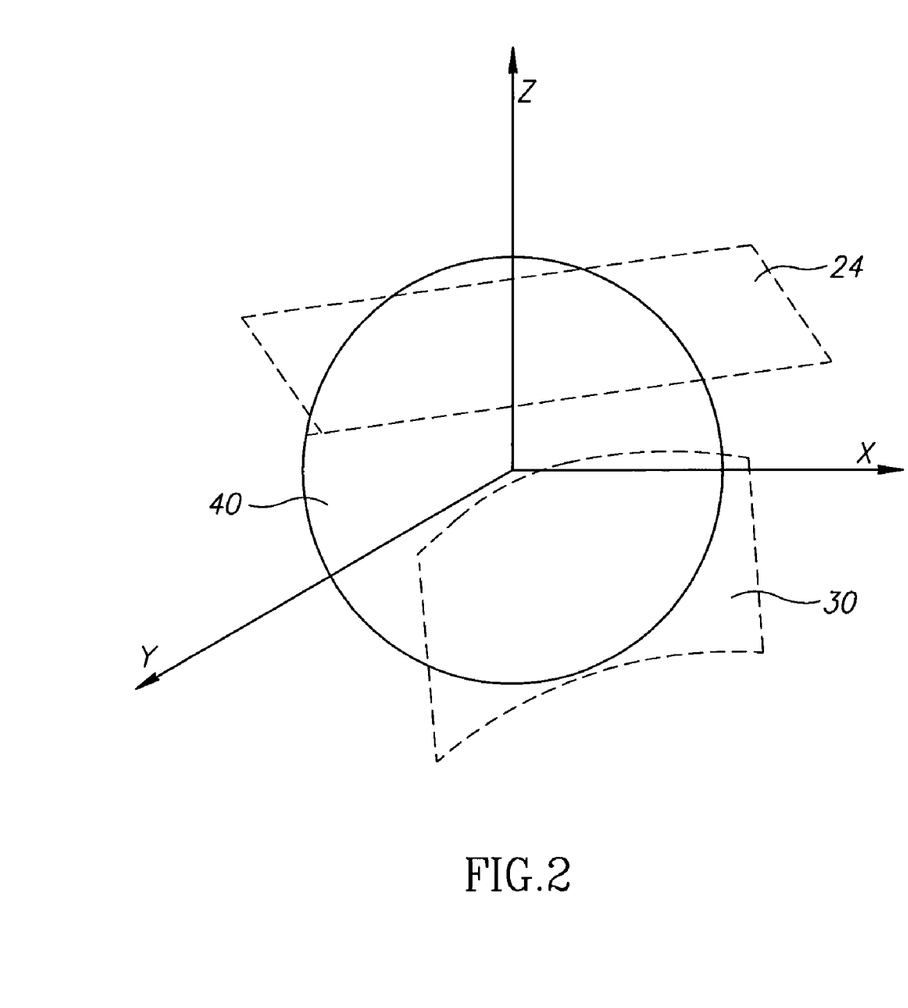
FIG. 2 is an axis diagram of a sphere from which contours of the endoprosthesis of FIGS. 1A and 1B may be cut in accordance with an embodiment of the present invention.

In accordance with a non-limiting embodiment of the invention, the contours 28 and 32 of the endoprosthesis 10 may be cut from a sphere or sphere-like shape 40 (referred to simply as sphere 40), shown in FIG. 2. The axis diagram of sphere 40 in FIG. 2 assists in understanding the various cross-sections in the figures illustrated hereinbelow.

Figure 3A:
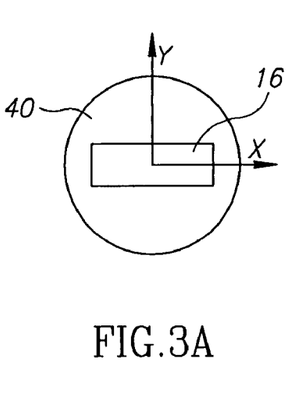
FIGS. 3A-3G are simplified illustrations of various shapes of articulating members of the endoprosthesis of the present invention, which may be fashioned from a sphere, as seen in the cross-section taken along the x-y plane.
Figure 3B:
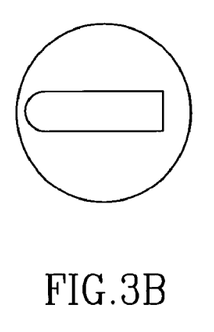
Figure 3C:
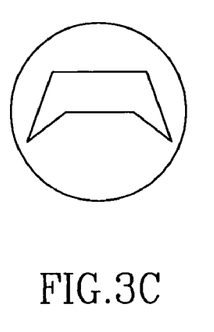
Figure 3D:
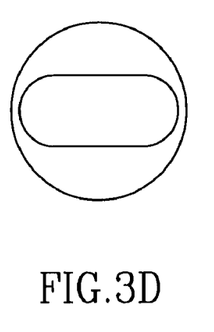
Figure 3E:
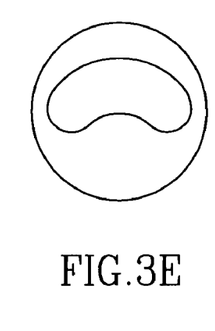
Figure 3F:
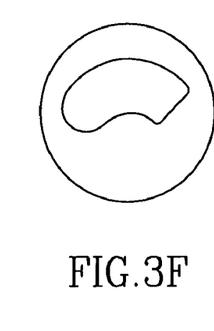
Figure 3G:
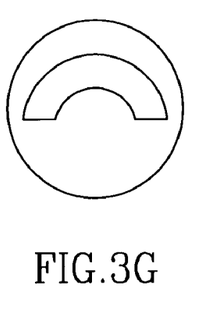

FIGS. 3A-3G illustrates various shapes of additional embodiments of articulating members 16 that may be fashioned from a sphere 40, as seen in the cross-section taken along plane x-y. FIG. 3A shows a rectangular or cylindrical contour. FIG. 3B shows a bullet-shaped contour. FIG. 3C shows a trapezoidal contour with pointy winged protrusions from the base of the trapezoid. FIG. 3D shows an oval or elliptical contour. FIG. 3E shows the banana shaped contour as shown in the embodiment of FIG. 1A. FIG. 3F shows the banana shaped contour as shown in the embodiment of FIG. 1A, but with a truncated end of the banana shape. FIG. 3G shows a semi-toroidal (semi-doughnut) contour.

Figure 4A:
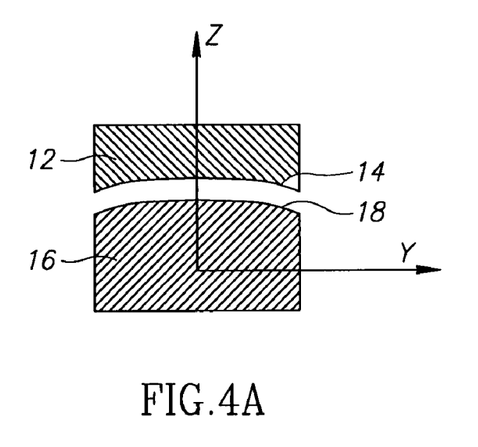
FIGS. 4A-4E are side section views of embodiments of the present invention, as seen in the section taken along the y-z plane.
Figure 4B:
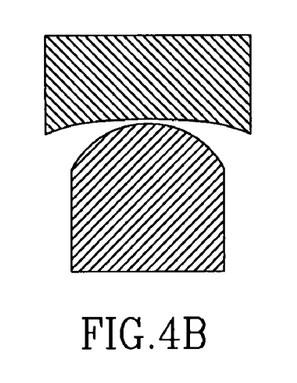
Figure 4C:
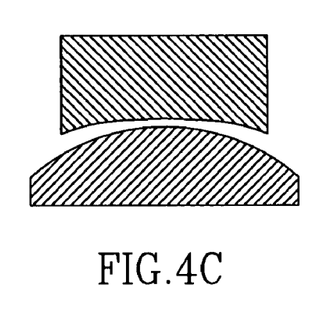

Various possible non-limiting examples of articulating embodiments are illustrated in FIGS. 4A-4E, as seen in the section taken along plane y-z. The generally concave first articulating surface 14 of first articulating member 12 may be fashioned to articulate in various degrees of matching opposing surfaces. FIG. 4A illustrates a relatively high degree of close matching surfaces (that is, the radii of curvature generally match or are identical and the contact areas also generally match or are identical) with each other along most of their respective articulating surfaces 18 and 14, respectively. FIG. 4B illustrates an example of one embodiment wherein respective articulating surfaces 18 and 14 are not closely matching, that is, the radii of curvature do not match. FIG. 4C is an illustration of an embodiment wherein articulating surfaces 18 and 14 are closely matching but where the areas of contact between articulating surfaces 18 and 14 are not the same.

Figure 4D:
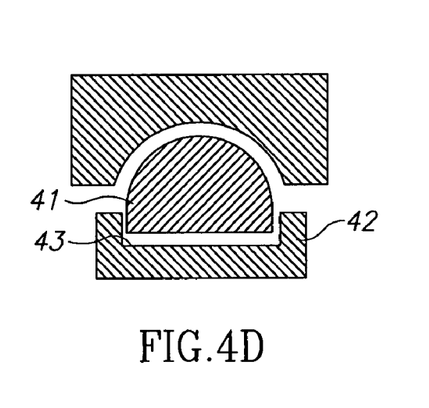
Figure 4E:
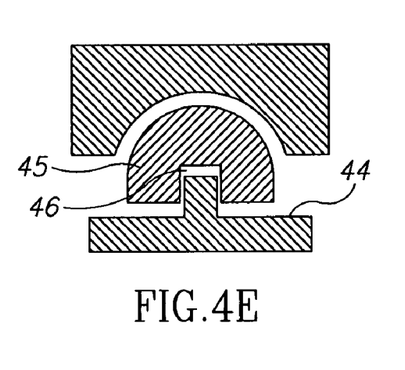
Figure 5A:
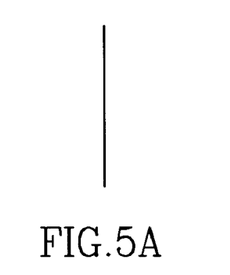
FIGS. 5A-5F are examples of cutting shapes that can create the shapes seen in FIGS. 3A-3G, as viewed along the z axis.
Figure 5B:
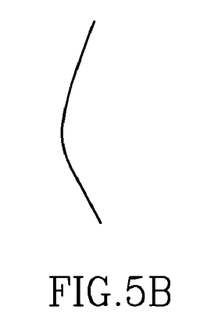
Figure 5C:
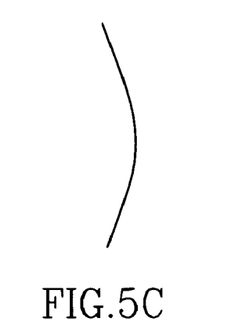
Figure 5D:
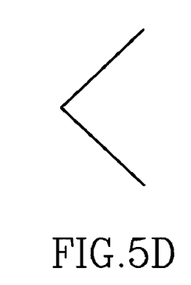
Figure 5E:
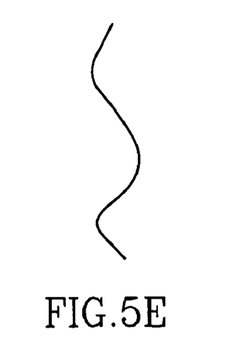
Figure 5F:
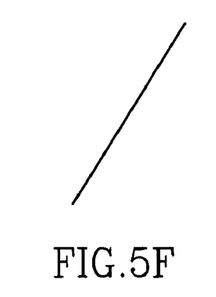

FIG. 4D is an illustration of an embodiment wherein one of the articulating members is constructed of two parts, an articulating portion 41 mounted in a recess 43 formed in an attachment portion 42. FIG. 4E is an illustration of an embodiment wherein one of the articulating members is constructed of two parts, an attachment portion 44 mounted in a recess 46 formed in an articulating portion 45.

Some examples of cutting shapes that create the shapes seen in FIGS. 3A-3G are illustrated in FIGS. 5A-5F, as viewed along the z-axis.

Figure 6A:
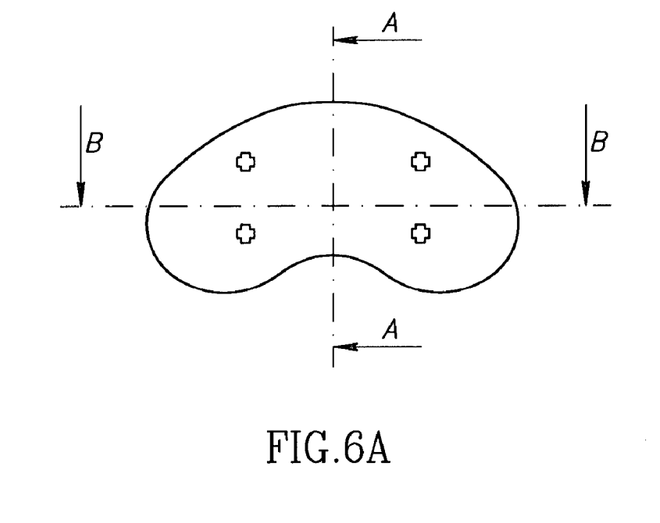
FIGS. 6A-6C are simplified illustrations of an endoprosthesis, constructed and operative in accordance with another embodiment of the present invention, wherein two articulation members articulate against a third articulation member.
Figure 6B:
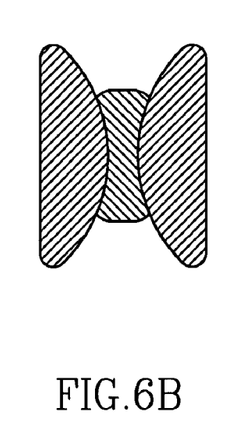
Figure 6C:
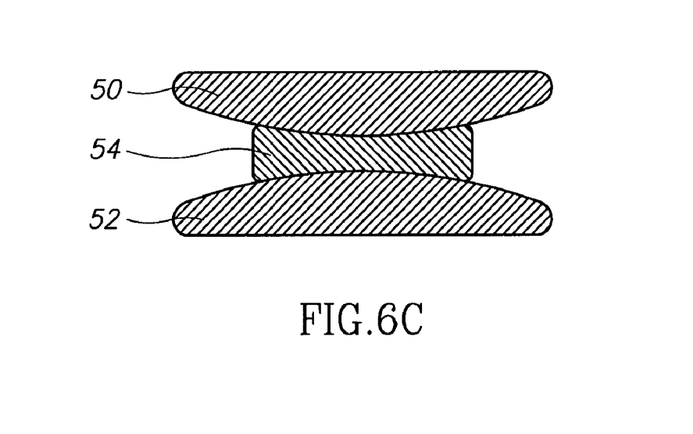

Reference is now made to FIGS. 6A-6C, which illustrate an endoprosthesis, constructed and operative in accordance with another embodiment of the present invention. In this embodiment, two articulation members 50 and 52 with generally planar attachment surfaces on their outer surfaces articulate against a third articulation member 54 on their inner surfaces. In the illustrated embodiment, the inner surfaces of articulation members 50 and 52 are shown as having a convex shape and opposing articulating surfaces of third articulation member 54 have a concave shape. It is to be understood, however, that any combination of opposing concave and convex surfaces according to this embodiment would be in the scope of the present invention. For example, the inner surfaces of articulation members 50 and 52 may have a concave shape and the opposing articulating surfaces of third articulation member 54 may have a convex shape.

Figure 7A:
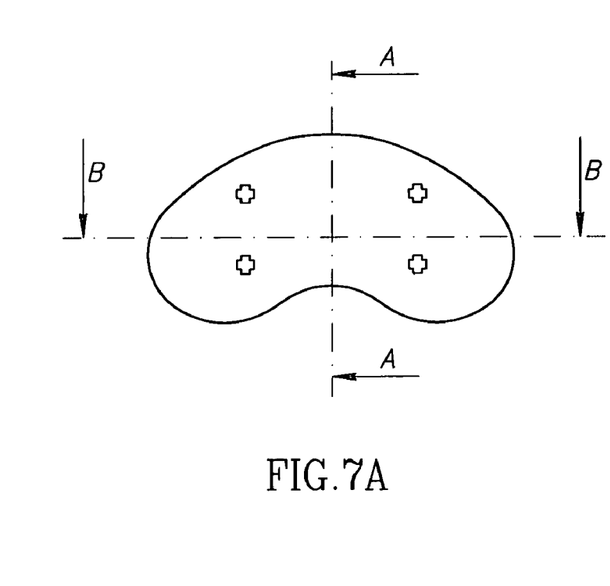
FIGS. 7A-7C are simplified illustrations of an endoprosthesis, constructed and operative in accordance with yet another embodiment of the present invention, which may be similar in construction to the endoprosthesis of FIGS. 6A-6C, except that the third articulation member may be constructed as a hollow member.
Figure 7B:
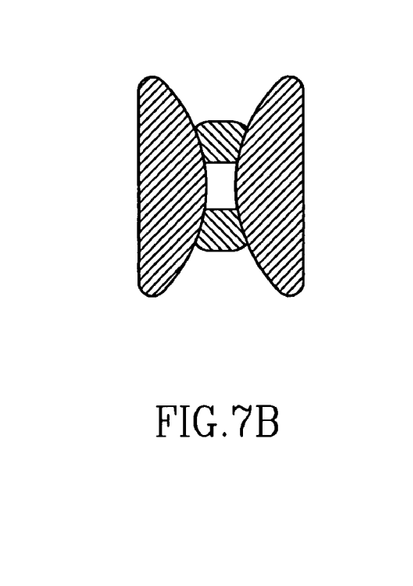
Figure 7C:
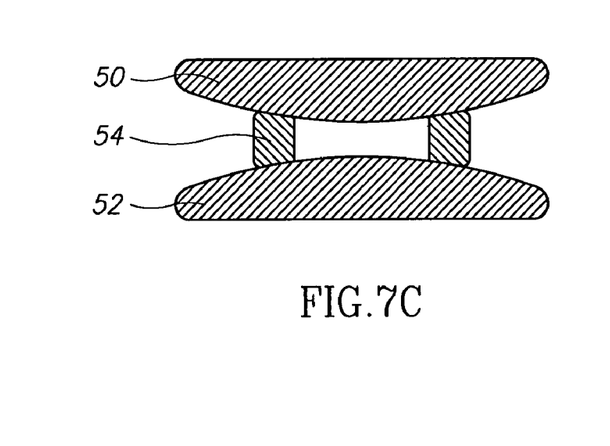

Reference is now made to FIGS. 7A-7C, which illustrate an endoprosthesis, constructed and operative in accordance with yet another embodiment of the present invention. The endoprosthesis of FIGS. 7A-7C may be similar in construction to the endoprosthesis of FIGS. 6A-6C, except that the third articulation member 54 may be constructed as a hollow member.

Figure 8A:
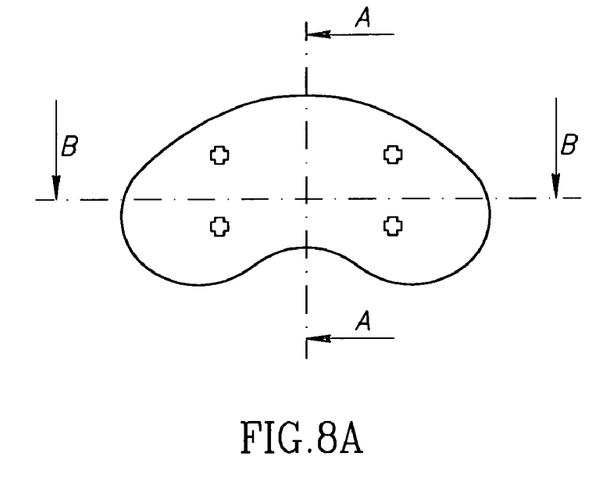
FIGS. 8A-8C are simplified illustrations of an endoprosthesis, constructed and operative in accordance with still another embodiment of the present invention, wherein a first articulation member comprises a plurality of bulbous articulation surfaces that articulate with a second articulation member.
Figure 8B:
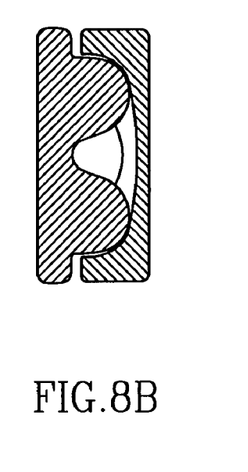
Figure 8C:
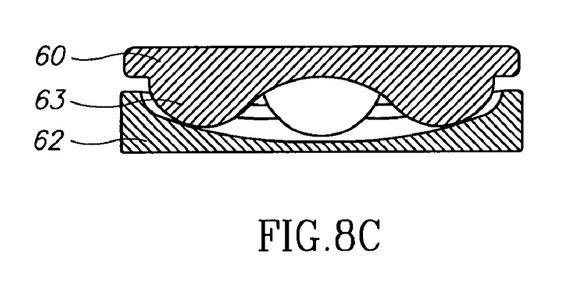

Reference is now made to FIGS. 8A-8C, which illustrate an endoprosthesis, constructed and operative in accordance with still another embodiment of the present invention. In this embodiment, a first articulation member 60 articulates with a second articulation member 62. The first articulation member 60 may comprise a plurality of bulbous articulation surfaces 63 which articulate with the generally concave second articulation member 62. The plurality of bulbous articulation surfaces 63 may provide additional degrees of rotational or other movement, such as but not limited to, flexion, extension and lateral bending.

Figure 9A:
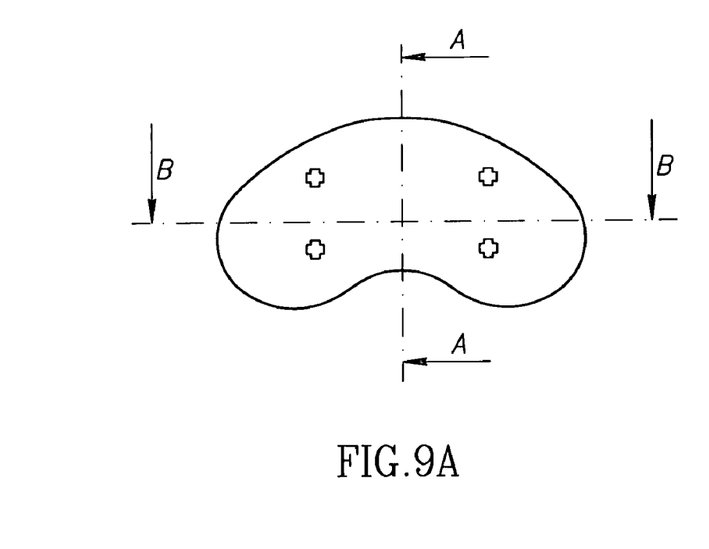
FIGS. 9A-9C are simplified illustrations of an embodiment similar to that of FIGS. 8A-8C, but with an additional elastomeric member between the first and second articulation members.
Figure 9B:
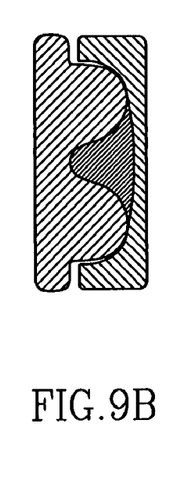
Figure 9C:
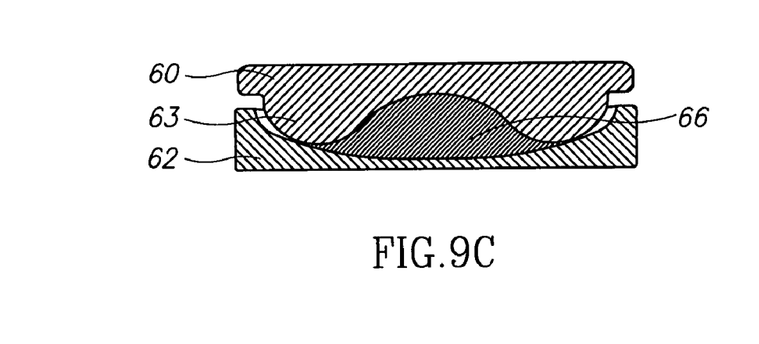

Reference is now made to FIGS. 9A-9C, which illustrate an embodiment similar to that of FIGS. 8A-8C, but with an additional elastomeric member 66 between first and second articulation members 60 and 62. Elastomeric member 66 is configured to add a cushioning effect to endoprosthesis 10.

Figure 10A:
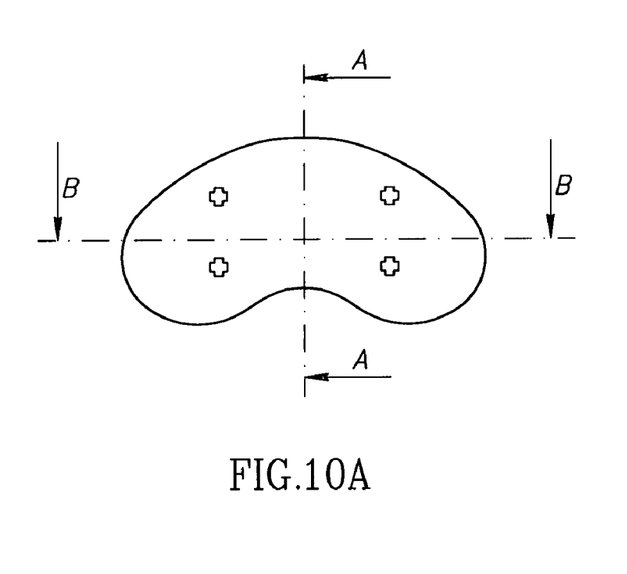
FIGS. 10A-10C are simplified illustrations of an endoprosthesis, constructed and operative in accordance with another embodiment of the present invention, wherein one of the articulation members is a varying height element.
Figure 10B:
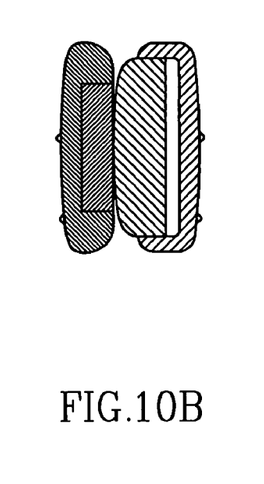
Figure 10C:
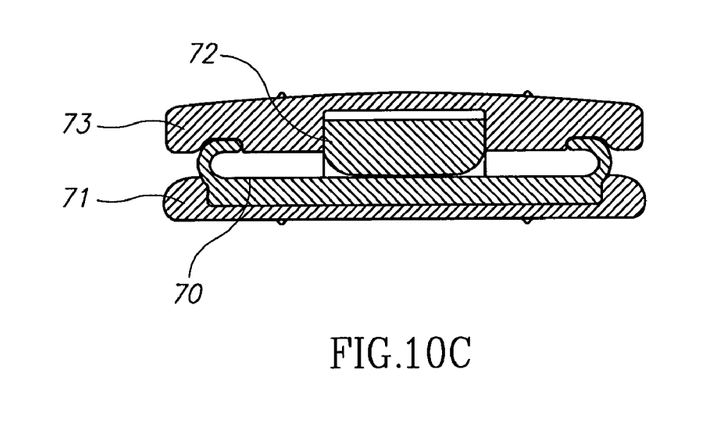

Reference is now made to FIGS. 10A-10C, which illustrate an endoprosthesis, constructed and operative in accordance with another embodiment of the present invention. In this embodiment, a first articulation member 70 is attached to or is integrally formed with an attachment member 71. A second articulation member 72 is attached to or is integrally formed with a second attachment member 73. The second articulation member 72 is a varying height element, that is, its protrusion from second attachment member 73 is adjustable. For example, the second articulation member 72 may include a screw which may be screwed up or down into second attachment member 73, thereby enabling adjusting the total thickness of the endoprosthesis. This may be useful as the space between adjacent vertebrae may vary from one individual to another.

Although the invention has been described in conjunction with specific embodiments thereof, it is evident that many alternatives, modifications and variations will be apparent to those skilled in the art. Accordingly, it is intended to embrace all such alternatives, modifications and variations.

What is claimed is:

1. An endoprosthesis comprising:
   a first articulating member formed with a generally concave articulating surface; and
   a second articulating member formed with a generally convex articulating surface which articulates with said concave articulating surface, said first and second articulating members each having a generally planar attachment surface for attachment to spine structure;
   wherein the first articulating member comprises a banana-shaped contour defined by a cutting surface that cuts through a portion of the first articulating member at a non-zero angle relative to its attachment surface, and the second articulating member comprises a banana-shaped contour defined by a cutting surface that cuts through a portion of the second articulating member at a non-zero angle relative to its attachment surface, wherein the generally concave articulating surface of said first articulation member is free of any bulbous articulation surfaces and the generally convex articulating surface of said second articulation member comprises a plurality of bulbous articulation surfaces which articulate with the generally concave articulating surface of said first articulation member, wherein the plurality of bulbous articulation surfaces share a common single articulating surface of said first articulation member.

2. The endoprosthesis according to claim 1, wherein said contours are defined by cutting a sphere.

3. The endoprosthesis according to claim 1, wherein radii of curvature of the first and second articulating members generally match.

4. The endoprosthesis according to claim 1, wherein radii of curvature of the first and second articulating members generally do not match.

5. The endoprosthesis according to claim 1, wherein contact areas of the first and second articulating members generally match.

6. The endoprosthesis according to claim 1, wherein contact areas of the first and second articulating members generally do not match.

7. The endoprosthesis according to claim 1, wherein one of the articulating members comprises an articulating portion mounted in a recess formed in an attachment portion.

8. The endoprosthesis according to claim 1, wherein one of the articulating members comprises an attachment portion mounted in a recess formed in an articulating portion.

9. The endoprosthesis according to claim 1, wherein the attachment surfaces comprise protrusions to improve attachment to the spine structure.

10. The endoprosthesis according to claim 1, further comprising an elastomeric member positioned between said first and second articulation members.

11. The endoprosthesis according to claim 10, wherein said elastomeric member fills a volume defined between the generally concave articulating surface of said first articulation member and the generally convex articulating surface of said second articulation member.

12. The endoprosthesis according to claim 10, wherein said elastomeric member does not overlap said bulbous articulation surfaces.

* * * * *